(12) United States Patent  
Adachi et al.

(10) Patent No.: US 8,172,748 B2  
(45) Date of Patent: May 8, 2012

(54) ELECTRIC BENDING ENDOSCOPE

(75) Inventors: Harutaka Adachi, Ome (JP); Masanobu Koitabashi, Hachioji (JP); Shoichi Amano, Hachioji (JP); Takashi Sawai, Hachioji (JP); Seigo Ito, Hachioji (JP); Atsushi Ogawa, Hachioji (JP)

(73) Assignee: Olympus Medical Systems Corp. (JP)

( * ) Notice: Subject to any disclaimer, the term of this patent is extended or adjusted under 35 U.S.C. 154(b) by 422 days.

(21) Appl. No.: 12/406,376

(22) Filed: Mar. 18, 2009

(65) Prior Publication Data

US 2009/0247829 A1    Oct. 1, 2009

(30) Foreign Application Priority Data

Mar. 31, 2008    (JP) .................. 2008-091917

(51) Int. Cl.
*A61B 1/00* (2006.01)
*A61B 1/04* (2006.01)
(52) U.S. Cl. ...................... 600/152; 600/110
(58) Field of Classification Search .................. 600/152, 600/136, 103, 133, 169, 111, 348, 921; 137/560; 348/71, 74
See application file for complete search history.

(56) References Cited

U.S. PATENT DOCUMENTS

| 4,609,247 | A | * | 9/1986 | Annoot | 439/591 |
| 6,099,465 | A | * | 8/2000 | Inoue | 600/134 |
| 2004/0073085 | A1 | | 4/2004 | Ikeda et al. | |
| 2004/0171913 | A1 | | 9/2004 | Saruya | |
| 2007/0060789 | A1 | * | 3/2007 | Uchimura et al. | 600/110 |
| 2007/0265498 | A1 | | 11/2007 | Ito | |

FOREIGN PATENT DOCUMENTS

JP    8-224206    9/1996

OTHER PUBLICATIONS

European Search Report dated Jul. 29, 2009 in corresponding European Patent Application No. EP 09 00 4747 (English language).
Letter from German associate dated Aug. 3, 2009 forwarding the European Search Report dated Jul. 29, 2009 to Japanese associate, including discussion of relevancy thereof. German associate's letter dated Aug. 3, 2009 was date stamped received by Japanese associate on Aug. 7, 2009 (English language).

* cited by examiner

*Primary Examiner* — Philip R Smith
*Assistant Examiner* — Ronald D Colque
(74) *Attorney, Agent, or Firm* — Ostrolenk Faber LLP

(57) ABSTRACT

An electric bending endoscope includes an elongate insertion portion provided with a bending portion, a drive unit, and an operation unit, wherein the drive unit and the operation unit respectively include a drive unit side electric contact portion and an operation unit side electric contact portion configured to be coupled to and separated from each other by moving the drive unit and the operation unit close to and apart from each other in a coupling and separation axial direction, and the drive unit and the operation unit includes a lock mechanism configured to lock and unlock the drive unit and the operation unit to and from each other with respect to the coupling and separating axial direction.

2 Claims, 12 Drawing Sheets

ELECTRIC BENDING ENDOSCOPE

CROSS-REFERENCE TO RELATED APPLICATIONS

This application is based upon and claims the benefit of priority from prior Japanese Patent Application No. 2008-091917, filed Mar. 31, 2008, the entire contents of which are incorporated herein by reference.

BACKGROUND OF THE INVENTION

1. Field of the Invention

The present invention relates to an electric bending endoscope wherein a bending portion of an insertion portion is configured to be electrically actuated to be bent.

2. Description of the Related Art

An electric bending endoscope is disclosed in Jpn. Pat. Appln. KOKAI Publication No. 8-224206. In this electric bending endoscope, a bending portion configured to be actuated to be bent is provided at the distal end portion of an elongate insertion portion configured to be inserted into a lumen. An operation portion configured to be held and operated by an operator is coupled to the proximal end portion of the insertion portion. Further, operation wires for the bending actuation of the bending portion are inserted through the insertion portion. The distal end portion of the operation wire is coupled to the distal end portion of the bending portion, and the proximal end portion of the operation wire is brought into the operation portion. The operation portion includes a built-in electric bending actuation mechanism, and the proximal end portion of the operation wire is connected to the electric bending actuation mechanism. Further, a bending operation switch box including bending operation switches is removably mounted to the operation portion. When the bending operation switch is operated, the electric bending actuation mechanism is actuated, and the operation wire is moved back and forth so that the bending portion is actuated to be bent.

BRIEF SUMMARY OF THE INVENTION

In an aspect of the present invention, an electric bending endoscope includes: an elongate insertion portion configured to be inserted into a lumen and provided with a bending portion configured to be actuated to be bent; a drive unit connected to a proximal end portion of the insertion portion and configured to generate a drive force to actuate the bending portion to be bend; and an operation unit configured to be held by an operator and operate at least a bending actuation of the bending portion, and the drive unit and the operation unit respectively include a drive unit side electric contact portion and an operation unit side electric contact portion configured to be coupled to and separated from each other by moving the drive unit and the operation unit close to and apart from each other in a coupling and separating axial direction, and the drive unit and the operation unit includes a lock mechanism configured to lock and unlock the drive unit and the operation unit to and from each other with respect to the coupling and separating axial direction.

In another aspect of the present invention, an elongate insertion portion is configured to be inserted into a lumen and provided with a bending portion configured to be actuated to be bent, a drive unit is connected to a proximal end portion of the insertion portion and configured to generate a drive force to actuate the bending portion to be bend, an operation unit is configured to be held by an operator and operate at least a bending actuation of the bending portion, and the drive unit includes: a drive unit side electric contact portion configured to be coupled to and separated from an operation unit side electric contact portion provided in the operation unit by moving the drive unit close to and apart from the operation unit in a coupling and separating axial direction; and a lock mechanism configured to lock and unlock the drive unit to and from the operation unit with respect to the coupling and separating axial direction.

In another aspect of the present invention, an elongate insertion portion is configured to be inserted into a lumen and provided with a bending portion configured to be actuated to be bent, a drive unit is connected to a proximal end portion of the insertion portion and configured to generate a drive force to actuate the bending portion to be bend, and an operation unit is configured to be held by an operator and operate at least a bending actuation of the bending portion, and the operation unit includes: an operation unit side electric contact portion configured to be coupled to and separated from a drive unit side electric contact portion provided in the drive unit by moving the operation unit close to and apart from the drive unit in a coupling and separating axial direction; and a lock mechanism configured to lock and unlock the operation unit to and from the drive unit with respect to the coupling and separating axial direction.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will hereinafter be described with reference to the drawings.

FIGS. 1 to 5 show a first embodiment of the present invention.

Figure 1:
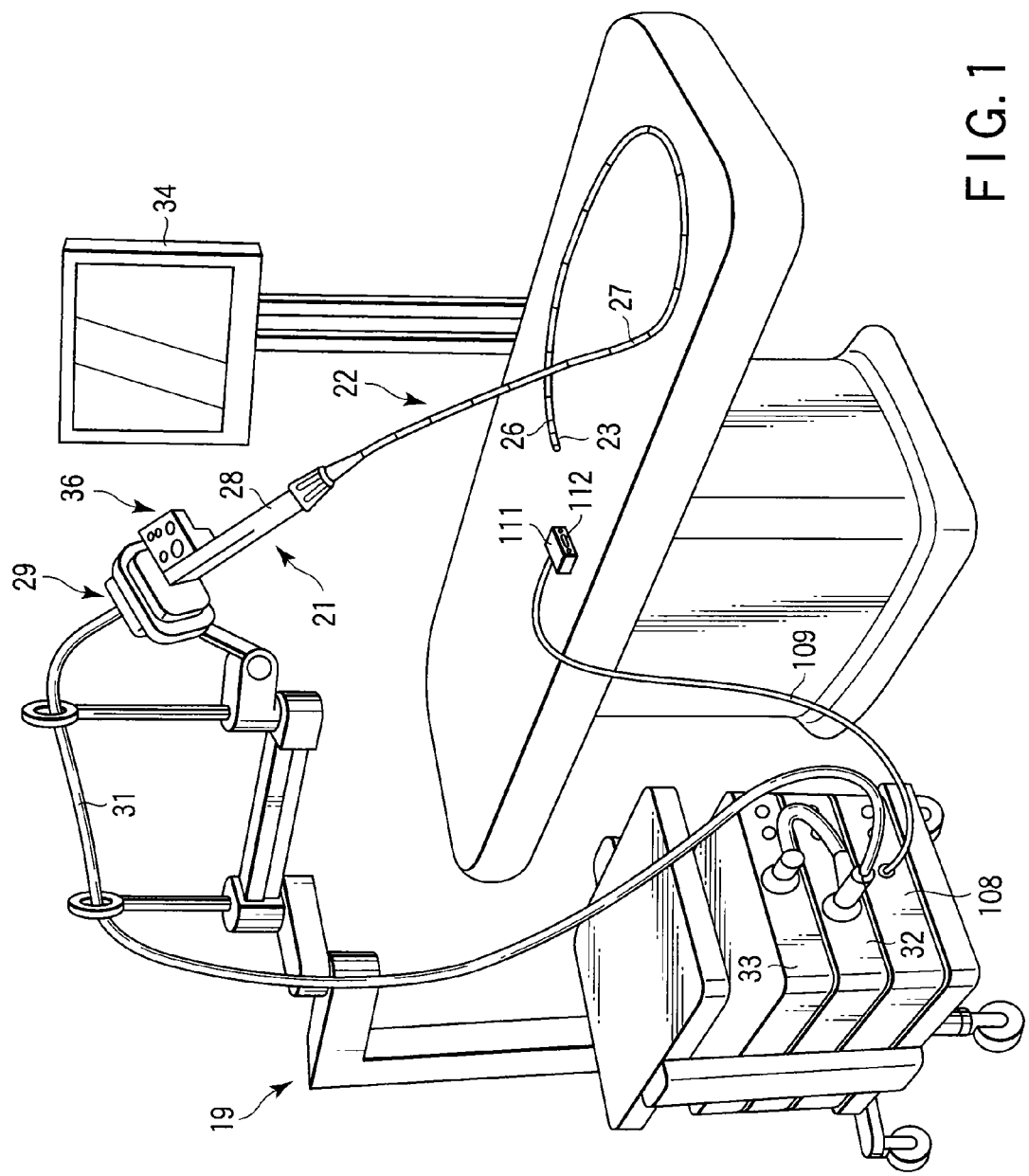
FIG. 1 is a perspective view showing an electric bending endoscope system according to a first embodiment of the present invention.
Figure 2A:
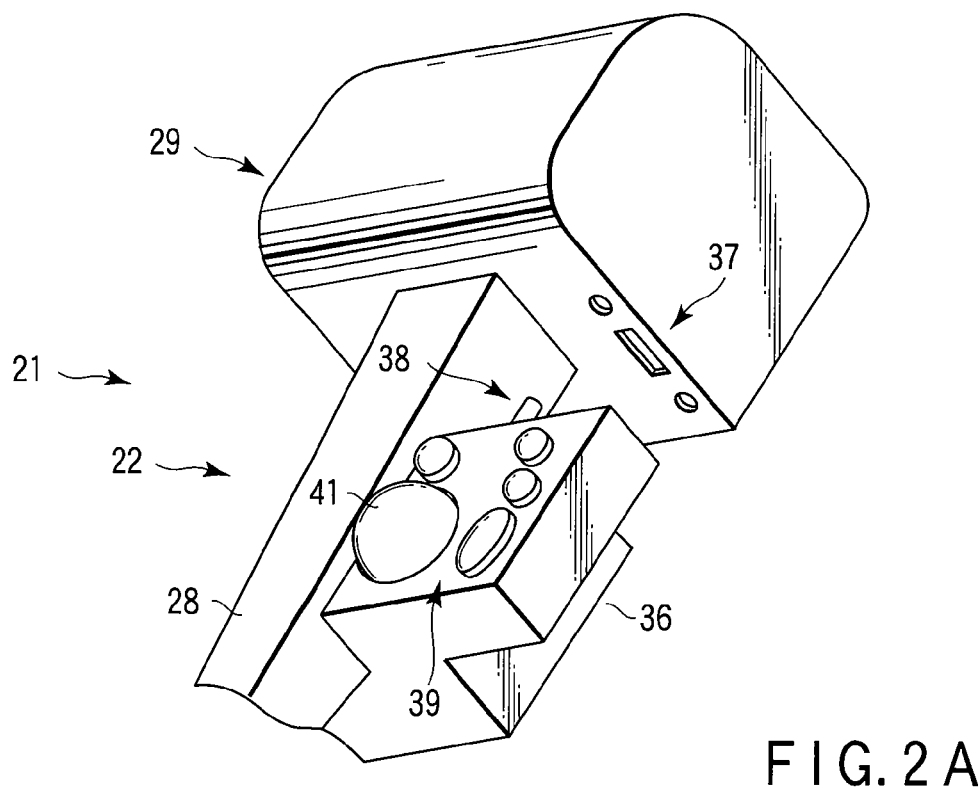
FIG. 2A is a perspective view showing an electric bending endoscope according to the first embodiment of the present invention in a separation state.
Figure 2B:
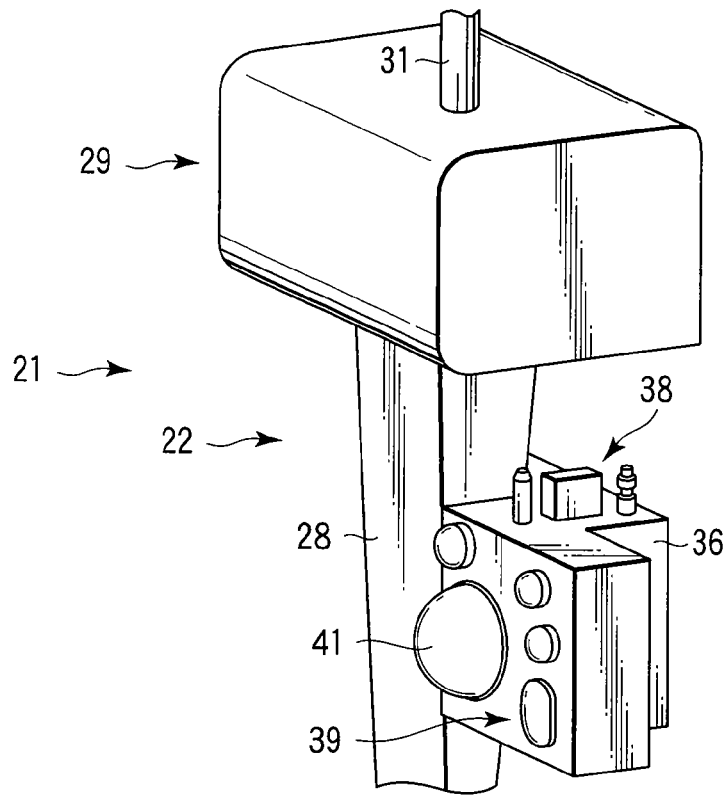
FIG. 2B is another perspective view showing the electric bending endoscope according to the first embodiment of the present invention in a separation state.

Referring to FIGS. 1 to 2B, in an electric bending endoscope system of the present embodiment, an electric bending endoscope 21 is movably and fixedly held by an endoscope holder 19.

The electric bending endoscope 21 includes an elongate insertion portion 22 configured to be inserted into the interior of the body. In the insertion portion 22, a distal end rigid portion 23, a bending portion 26 configured to be actuated to be bent, a long flexible insertion tube portion 27, and an insertion portion coupling portion 28 is provided from the distal end side to the proximal end side. The proximal end portion of the insertion portion coupling portion 28 is coupled to a motor unit 29 as a drive unit, and a universal cord 31 extends from the motor unit 29 and is connected to a light source device 32 and a video processor 33. The distal end rigid portion 23 of the insertion portion 22 includes a built-in illumination optical system. The illumination optical system is connected to the light source device 32 via a light guide inserted through the endoscope 21. Illumination light generated in the light source device 32 is supplied to the illumination optical system via the light guide, and the illumination light is applied to an observation target from the illumination optical system. Further, the distal end rigid portion 23 includes a built-in image pick-up unit. The image pick-up unit is connected to the video processor 33 via an electric cable inserted through the endoscope 21. The image pick-up unit is driven by the video processor 33 so that an observation image is picked up, and then an image signal obtained in the image pick-up unit is output to the video processor 33 so that the observation image is displayed on a monitor 34. Further, operation wires for the bending actuation of the bending portion 26 are inserted through the insertion portion 22. The distal end portion of the operation wire is coupled to the distal end portion of the bending portion 26, and the proximal end portion of the operation wire is connected to a drive mechanism in the motor unit 29. When the operation wire is operated to move back and forth by the drive mechanism, the bending portion 26 is actuated to be bent.

An operation unit 36 for operating the endoscope 21 is configured to be connected to and separated from the motor unit 29. That is, the motor unit 29 and the operation unit 36 are provided with a motor unit side connection portion 37 and an operation unit side connection portion 38 configured to be connected to and separated from each other, respectively. The operation unit 36 is also provided with various switches 39 for operating the illuminating and observing actuations, a track ball 41 for operating the bending actuation of the bending portion 26, etc.

A connection and separation mechanism is described with reference to FIGS. 3A to 5.

An electric connection mechanism of the connection and separation mechanism is described with reference to FIGS. 3A to 3C and FIGS. 4A and 4B.

In the operation unit side connection portion 38, a thick plate shaped plug 43 protrudes through an operation unit housing 42. In addition, a watertight member such as an 0-ring is provided between the operation unit housing 42 and the plug 43. A number of plug contacts 44 are provided on the axially outer end sides of both wide side surfaces of the plug 43. On the other hand, in the motor unit side connection portion 37, a plug insertion hole 47 is formed through a motor unit housing 46. A receptacle 48 is provided on the inside with respect to the plug insertion hole 47. The plug 43 of the operation unit side connection portion 38 is configured to be inserted into and pulled out from the receptacle 48 via the plug insertion hole 47. The direction in which the plug 43 is inserted into and pulled out from the receptacle 48 is hereinafter referred to as a connecting and separating axial direction as a coupling and separating axial direction. In addition, the receptacle 48 is held by a floating mechanism and is floatable in a plane perpendicular to the connecting and separating axial direction. In the floating mechanism, a cover 51 is fixed to a support portion 49 protruding from the inner surface of the motor unit housing 46, and the receptacle 48 is floatably held by the support portion 49 and the cover 51. A number of receptacle contacts 50 are provided within the receptacle 48. When the plug 43 is inserted into the receptacle 48, the plug contacts 44 of the plug 43 are brought into contact with the receptacle contacts 50 of the receptacle 48. Further, the receptacle 48 is provided with wipers 52 protruding into the inner cavity of the receptacle 48. The wiper 52 is configured to slide on the surface of the plug 43 in conjunction with the inserting action of the plug 43 into the receptacle 48, and remove water drops on the surface of the plug 43.

A lock mechanism of the connection and separation mechanism is described with reference to FIGS. 3A to 3C, and FIG. 5.

The lock mechanism is formed by a lock pin 53 as a lock portion of the operation unit side connection portion 38 and a lock receiving mechanism 54 of the motor unit side connection portion 37.

That is, in the operation unit side connection portion 38, a columnar shaped lock pin 53 protrudes through the operation unit housing 42 in the connecting and separating axial direction. In addition, a watertight member such as an 0-ring is provided between the operation unit housing 42 and the lock pin 53. The lock pin 53 is formed of an outer small outside diameter portion on the axially outer end thereof, and an inner large outside diameter portion on the axially inner end side thereof. A step between the outer small outside diameter portion and the inner large outside diameter portion has an axially inwardly and radially outwardly tapered shape, and forms a pin drive surface 56. Further, a groove shaped engagement receiving portion 57 circumferentially extends on the axially outer end portion of the inner large outside diameter portion of the lock pin 53. The side surface on the axially outer end side of the engagement receiving portion 57 is axially inwardly and radially inwardly inclined, and forms a pin retraction surface 58.

In the lock receiving mechanism 54, a lock pin insertion hole 59 is formed through the motor unit housing 46. An inner cylinder 61 as a lock receiving portion is provided on the inside with respect to the lock pin insertion hole 59 and extends in the connecting and separating axial direction. The inner cylinder 61 includes an outer large outside diameter portion on the axially outer end side thereof, a middle small inside diameter portion on the axially middle potion thereof, and an inner large inside diameter portion on the axially inner end side thereof. The outer large outside diameter portion of the inner cylinder 61 is fixed to the motor unit housing 46. When the operation unit 36 is moved with respect to the motor unit 29 in a connecting and separating axial direction, the lock pin 53 of the operation unit side connection portion 38 is inserted into and pulled out from the inner cylinder 61 via the lock pin insertion hole 59. The axially inner position of the lock pin 53 when completely inserted into the inner cylinder 61 is referred to as a connection position.

Container holes 62 radially perforate the middle small inside diameter portion of the inner cylinder 61. A steel ball 63 as an engaging member is radially slidably contained in each of the container holes 62. When the lock pin 53 is disposed at the connection position, the engagement receiving portion 57 of the lock pin 53 is aligned with the radial inside of the container hole 62 so that the steel ball 63 is enabled to be engaged with and disengaged from the engagement receiving portion 57 of the lock pin 53. The steel ball 63 is configured to be located at a radial inside engaging position where the steel ball 63 is engaged with the engagement receiving portion 57 and a radial outside retraction position where the steel ball 63 is disengaged from the engagement receiving portion 57.

The lock receiving mechanism 54 includes a holding mechanism configured to hold the steel ball 63 at the retraction position. That is, a stop cylinder 64 is coaxially mounted within the inner cylinder 61. The stop cylinder 64 includes a middle large outside diameter portion on the axially middle portion thereof disposed in the inner large inside diameter portion of the inner cylinder 61, and an outer small outside diameter portion on the axially outer end side thereof. The middle large outside diameter portion of the stop cylinder 64 is slidable along the inner peripheral surface of the inner large inside diameter portion of the inner cylinder 61, and so the stop cylinder 64 is axially movable with respect to the inner cylinder 61. Here, a bearing cap 65 covers the axially inner end portion of the inner cylinder 61. A coil shaped inside elastic member 67 is compressively provided between the bearing cap 65 and the middle large outside diameter portion of the stop cylinder 64, and the stop cylinder 64 is constantly axially outwardly urged with respect to the inner cylinder 61. An inner step portion is formed in the inner peripheral portion of the inner cylinder 61 between the inner large inside diameter portion and the middle small inside diameter portion. When the middle large outside diameter portion of the stop cylinder 64 is in contact with the inner step portion of the inner cylinder 61, the axially outward movement of the stop cylinder 64 is limited. The axially outer position of the stop cylinder 64 is referred to as a separation position. Here, a stop cylinder holding surface 68 is formed by the outer peripheral surface of the outer small outside diameter portion of the stop cylinder 64. That is, when the stop cylinder 64 is disposed at the separation position, the outer small outside diameter portion of the stop cylinder 64 is inserted in the middle small inside diameter portion of the inner cylinder 61, and the steel ball 63 within the container hole 62 is held at the retraction position by the stop cylinder holding surface 68. The state where the steel ball 63 is held at the retraction position is referred to as the hold state of the holding mechanism. Here, the outer end surface of the outer small outside diameter portion of the stop cylinder 64 is axially outwardly and radially outwardly inclined, and forms a stop cylinder drive surface 69. That is, when the lock pin 53 of the operation unit side connection portion 38 is inserted into the inner cylinder 61, the outer small outside diameter portion of the lock pin 53 is inserted in the outer small outside diameter portion of the stop cylinder 64, and the pin drive surface 56 of the lock pin 53 is in contact with the stop cylinder drive surface 69 of the stop cylinder 64, and the stop cylinder 64 is axially inwardly moved from the separation position together with the lock pin 53. The axially inner position of the stop cylinder 64 when the lock pin 53 is disposed at the connection position is referred to as a connection position. When the stop cylinder 64 is disposed at the connection position, the outer small outside diameter portion of the stop cylinder 64 is pulled out from the middle small inside diameter portion of the inner cylinder 61 and disposed in the inner large inside diameter portion of the inner cylinder 61, and the stop cylinder holding surface 68 of the stop cylinder 64 does not hold the steel ball 63. The state where the steel ball 63 is freed is referred to as the free state of the holding mechanism. Thus, the stop cylinder 64 and the inside elastic member 67 forms the holding mechanism, and the pin drive surface 56 of the lock pin 53 forms a free mechanism for switching the holding mechanism from the hold state to the free state.

The lock receiving mechanism 54 includes an urging mechanism urging the steel ball 63 toward the engaging position. That is, an outer cylinder 71 is coaxially mounted to the outside of the inner cylinder 61. The outer cylinder 71 includes an inner large inside diameter portion on the axially inner end side thereof, and an outer small inside diameter portion on the axially outer end side thereof. A step portion is formed between the inner large inside diameter portion and the outer small inside diameter portion of the outer cylinder 71. The outer small inside diameter portion of the outer cylinder 71 is slidable on the outer peripheral surface of the inner cylinder 61, so that the outer cylinder 71 is axially movable with respect to the inner cylinder 61. A coil shaped outside elastic member 66 is compressively provided between the bearing cap 65 and the step portion of the outer cylinder 71, and the outer cylinder 71 is constantly axially outwardly urged with respect to the inner cylinder 61. An axially outwardly and radially outwardly inclined outer cylinder urging surface 73 is formed on the inner peripheral side of the axially outer end portion of the outer cylinder 71. When the stop cylinder 64 is at the separation position and the steel ball 63 is held at the retraction position by the stop cylinder holding surface 68 of the stop cylinder 64, the outer cylinder urging surface 73 of the outer cylinder 71 is in contact with the steel ball 63, and the outer cylinder 71 is held at the axially inside separation position. When the holding of the steel ball 63 by the stop cylinder holding surface 68 of the stop cylinder 64 is released, the steel ball 63 is moved from the retraction position to the engaging position by the outer cylinder urging surface 73 due to the urging by the outside elastic member 66, and the outer cylinder 71 is moved from the separation position to the axially outside connection position. Here, an outer step portion is formed in the outer peripheral portion of the inner cylinder 61 between the outer large outside diameter portion and the middle small inside diameter portion of the inner cylinder 61. When the outer end of the outer cylinder 71 is in contact with the outer step portion of the inner cylinder 61, axially outward movement of the outer cylinder 71 is limited. The axially outer position of the outer cylinder 71 is referred to as a connection position. Here, the inner peripheral surface of the outer small inside diameter portion of the outer cylinder 71 forms an outer cylinder holding surface 74. That is, when the outer cylinder 71 is disposed at the connection position, the steel ball 63 is urged toward and held at the engaging position by the outer cylinder holding surface 74 of the outer cylinder 71. Thus, the bearing cap 65, the outer cylinder 71 and the outside elastic member 66 forms the urging mechanism.

The lock receiving mechanism 54 includes a release mechanism for releasing the urging to the steel ball 63 by the urging mechanism. That is, a release button 76 is provided and configured to project and depress in the motor unit 29. The release button 76 is slidable in the radial direction of the inner cylinder 61 and the outer cylinder 71, and is configured to be disposed at the radially outside connection position and the radially inside separation position. That is, a button cap 77 of the release button 76 is provided and configured to project and depress in the motor unit housing 46 in the radial direction of the inner cylinder 61 and the outer cylinder 71. A button shaft 78 protrudes from the radially inner end portion of the button cap 77. On the other hand, a bearing portion 79 axially protrudes from the axially inner end surface of the bearing cap 65, and a bearing hole 81 radially perforates the bearing portion 79. The button shaft 78 radially extends and is radially slidably inserted through the bearing hole 81. A radially inwardly and axially outwardly inclined shaft drive surface 82 is formed in the radially inner end portion of the button shaft 78. On the other hand, an outer cylinder arm portion 83 is provided in the axially outer end portion of the outer cylinder 71 and radially extends across the bearing cap 65. An outer cylinder drive surface 84 is formed in the outer cylinder arm portion 83 opposite to the release button 76, and the outer cylinder drive surface 84 is radially outwardly and axially inwardly inclined and is in contact with the shaft drive surface 82 of the button shaft 78. When the release button 76 is radially inwardly moved from the connection position to the separation position, the outer cylinder drive surface 84 of the outer cylinder arm portion 83 slides along the shaft drive surface 82 of the button shaft 78, and the outer cylinder 71 is axially inwardly moved from the connection position to the separation position. When the outer cylinder 71 is disposed at the separation position, the holding of the steel ball 63 by the outer cylinder holding surface 74 of the outer small inside diameter portion of the outer cylinder 71 is released so that the steel ball 63 is enabled to move to the retraction position where the steel ball 63 comes in contact with the outer cylinder urging surface 73. Thus, the release button 76 and the outer cylinder arm portion 83 forms the release mechanism.

When the lock pin 53 is pulled out from the inner cylinder 61, the steel ball 63 is moved from the engaging position to the retraction position by the pin retraction surface 58 of the lock pin 53. Thus, the pin retraction surface 58 forms a retraction mechanism.

Figure 3A:
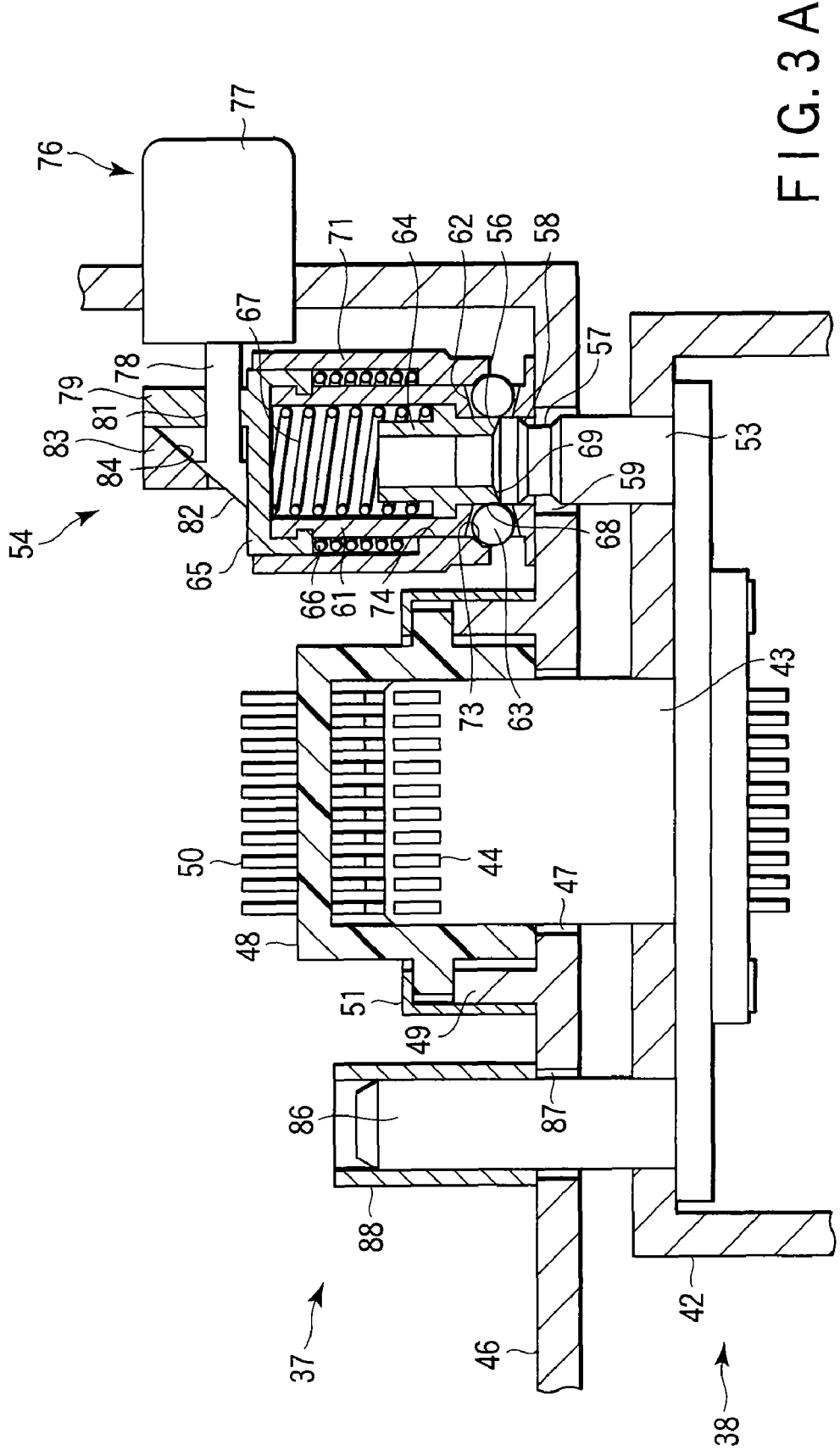
FIG. 3A is a partial longitudinal sectional side view showing a connection and separation mechanism according to the first embodiment of the present invention in a separation state.

A rotation limitation mechanism of the connection and separation mechanism is described with reference to FIGS. 3A to 3B.

The rotation limitation mechanism includes the lock pin 53 as a first limitation member of the operation unit side connection portion 38, and the inner cylinder 61 as a first limitation receiving member of the motor unit side connection portion 37. Further, in the rotation limitation mechanism, a cylindrical limitation pin 86 as a second limitation member protrudes through the operation unit housing 42 in the connecting and separating axial direction in the operation unit side connection portion 38. A watertight member such as an O-ring is provided between the operation unit housing 42 and the limitation pin 86. The limitation pin 86 is disposed opposite to the lock pin 53 with respect to the plug 43. On the other hand, in the motor unit side connection portion 37, a limitation pin insertion hole 87 is formed through the motor unit housing 46. A cylindrical pin receiving portion 88 as a second limitation receiving member is provided on the inside with respect to the limitation pin insertion hole 87 and extends in the connecting and separating axial direction. The outer end portion of the pin receiving portion 88 is fixed to the inner surface of the motor unit housing 46. When the operation unit 36 is moved with respect to the motor unit 29 in the connecting and separating axial direction, the limitation pin 86 of the operation unit side connection portion 38 is inserted into and pulled out from the pin receiving portion 88 via the limitation pin insertion hole 87. When the lock pin 53 is inserted into the inner cylinder 61 and the limitation pin 86 is inserted into the pin receiving portion 88, the rotation of the lock pin 53 around the connecting and separating axis is limited by the inner cylinder 61 and the rotation of the limitation pin 86 around the same is limited by the pin receiving portion 88, so that the rotation of the operation unit 36 with respect to the motor unit 29 around the same is limited.

Next, the method of using the electric bending endoscope 21 in the present embodiment is described.

Referring to FIGS. 3A and 3B and FIGS. 4A and 4B, in order to connect the operation unit 36 to the motor unit 29, the operation unit 36 is moved close to the motor unit 29 in the connecting and separating axial direction. As a result, the plug 43 of the operation unit side connection portion 38 is inserted into and connected to the receptacle 48 of the motor unit side connection portion 37. At this moment, water drops on the surface of the plug 43 are removed by the wiper 52 of the receptacle 48. At the same time, the lock pin 53 of the operation unit side connection portion 38 is inserted into the inner cylinder 61 of the motor unit side connection portion 37 up to the connection position. At this point, the outer small outside diameter portion of the lock pin 53 is inserted in the outer small outside diameter portion of the stop cylinder 64, the pin drive surface 56 of the lock pin 53 is in contact with the stop cylinder drive surface 69 of the stop cylinder 64, and the stop cylinder 64 is axially inwardly moved by the lock pin 53 from the separation position to the connection position against the urging by the inside elastic member 67. Then, the outer small outside diameter portion of the stop cylinder 64 is pulled out from the middle small inside diameter portion of the inner cylinder 61, and the holding of the steel ball 63 by the stop cylinder holding surface 68 of the stop cylinder 64 at the retraction position is released. When the holding of the steel ball 63 by the stop cylinder holding surface 68 is released and then the lock pin 53 is disposed at the connection position, the outer cylinder 71 is axially outwardly moved due to the urging by the outside elastic member 66 so that the steel ball 63 is radially inwardly moved from the retraction position to the engaging position by the outer cylinder urging surface 73 of the outer cylinder 71 and engaged with the engagement receiving portion 57, and then outer cylinder 71 is moved to the connection position so that the steel ball 63 is held at the engaging position by the outer cylinder holding surface 74 of the outer cylinder 71. In addition, when the outer cylinder 71 is axially outwardly moved from the separation position to the connection position, the shaft drive surface 82 of the button shaft 78 slides on the outer cylinder drive surface 84 of the outer cylinder arm portion 83, the button shaft 78 is radially outwardly moved from the separation position to the connection position, and then the release button 76 is disposed at the connection position. Thus, the lock pin 53 is locked to the lock receiving mechanism 54. Further, simultaneously with the insertion of the lock pin 53 into the inner cylinder 61, the limitation pin 86 of the operation unit side connection portion 38 is inserted into the pin receiving portion 88 of the motor unit side connection portion 37.

In the state where the operation unit 36 is connected to the motor unit 29, the various switches 39 and the track ball 41 of the operation unit 36 are operated so that the endoscope 21 is actuated, observation of the interior of the body, for example, is carried out. At this point, the operation unit 36 is not moved apart from the motor unit 29 because the operation unit 36 is locked to the motor unit 29 with respect to the connecting and separating axial direction, and the operation unit 36 is not rotated with respect to the motor unit 29 because the rotation of the operation unit 36 with respect to the motor unit 29 around the connecting and separating axis is limited. Particularly, since the operation unit 36 is firmly fixed to the motor unit 29, the whole endoscope 21 held by the endoscope holder 19 is movable by holding and moving the operation unit 36.

Figure 3B:
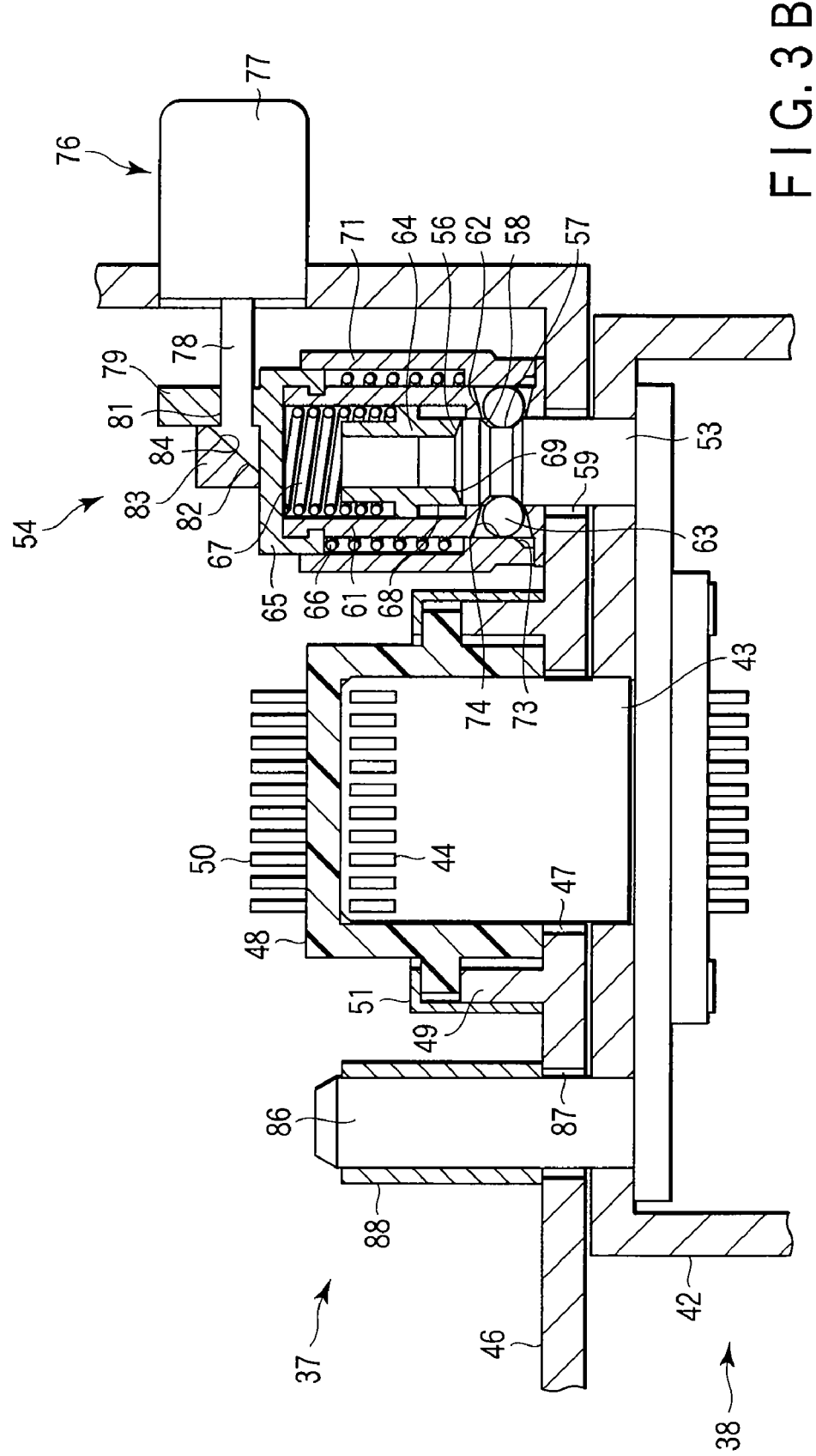
FIG. 3B is a partial longitudinal sectional side view showing the connection and separation mechanism according to the first embodiment of the present invention in a connection state.
Figure 3C:
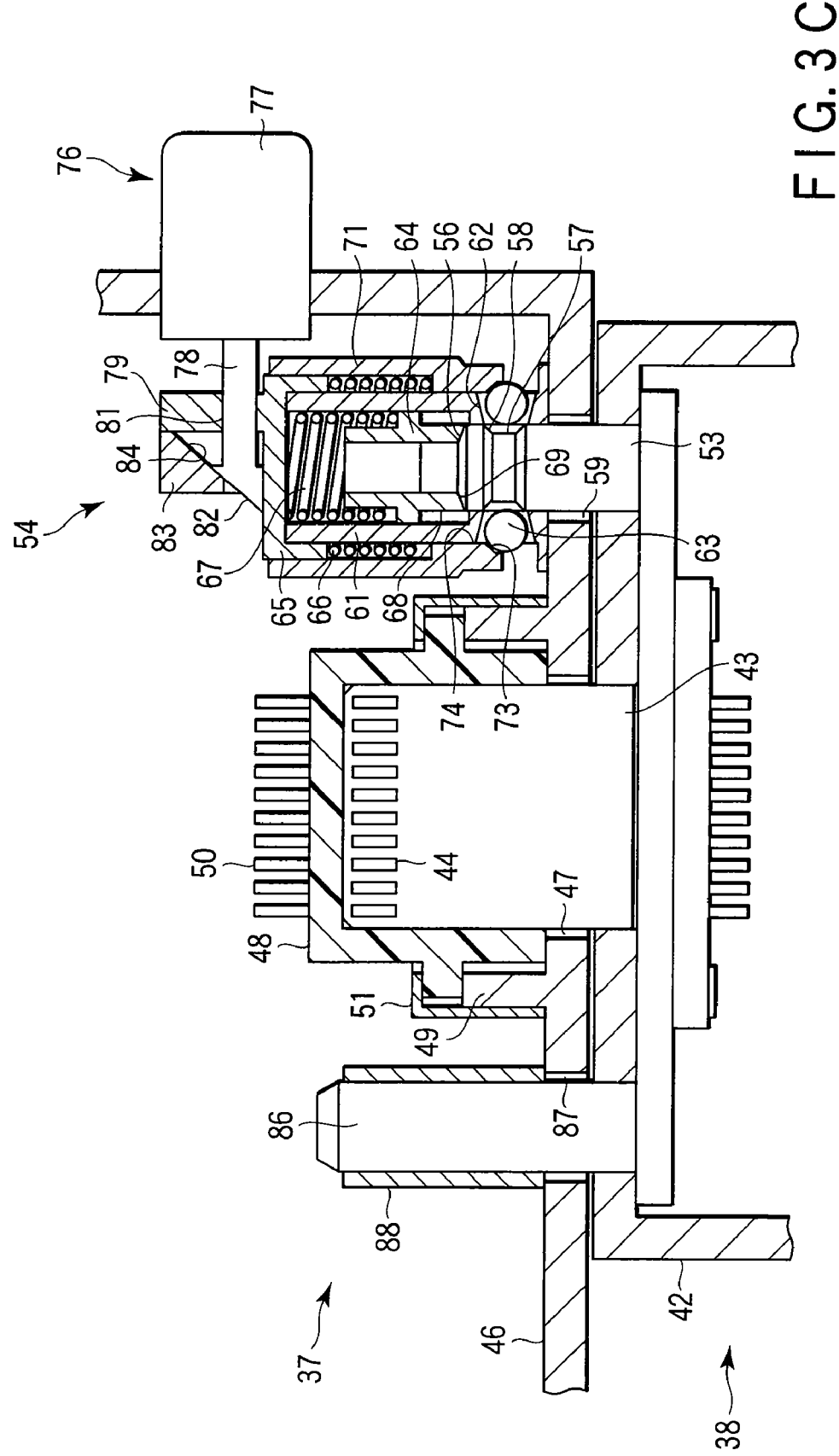
FIG. 3C is a partial longitudinal sectional side view showing the connection and separation mechanism according to the first embodiment of the present invention in a release state.
Figure 4A:
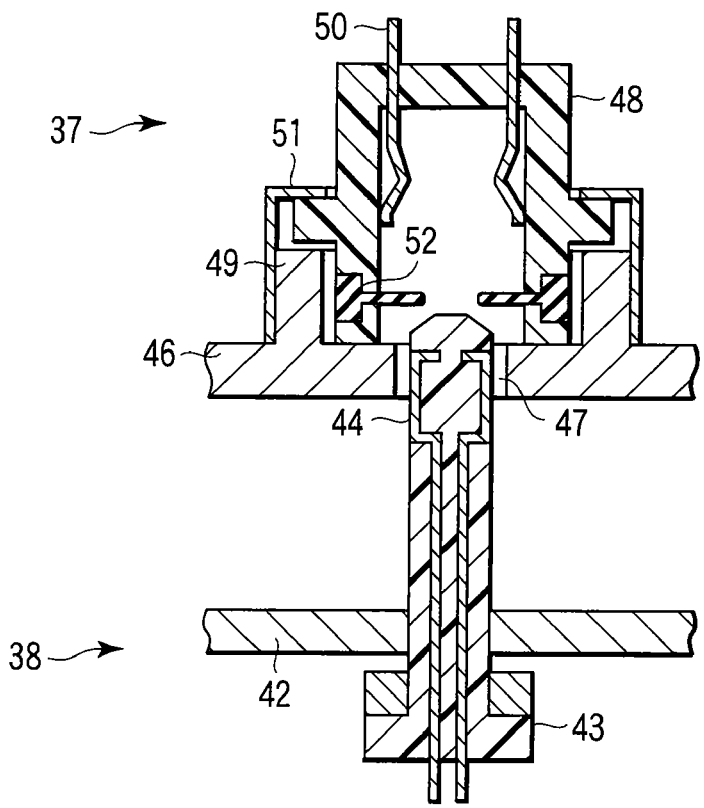
FIG. 4A is a longitudinal sectional view showing an electric connection mechanism according to the first embodiment of the present invention in a separation state.
Figure 4B:
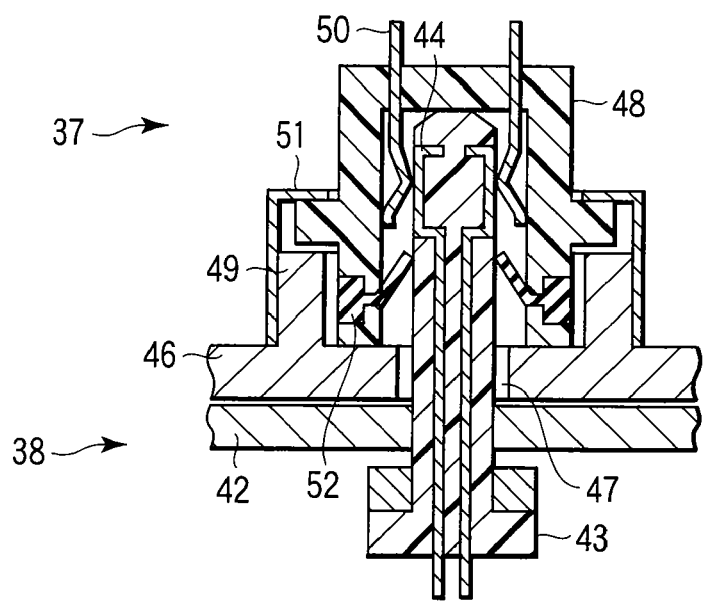
FIG. 4B is a longitudinal sectional view showing the electric connection mechanism according to the first embodiment of the present invention in a connection state.
Figure 5:
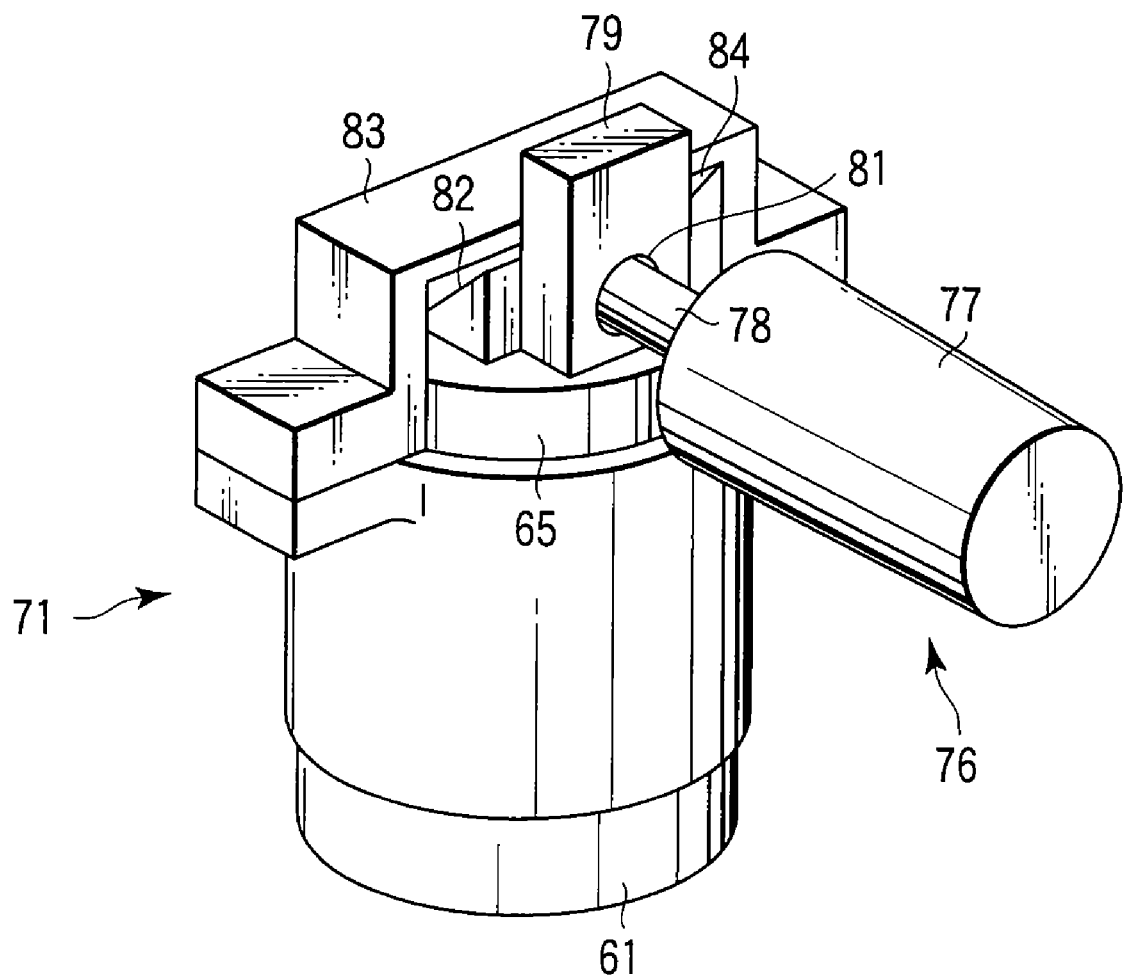
FIG. 5 is a perspective view showing a release mechanism according to the first embodiment of the present invention.

Referring to FIGS. 3B and 3C, in order to enable the operation unit 36 to be moved apart from the motor unit 29, the release button 76 of the motor unit 29 is depressed and kept as it is. At this point, the button shaft 78 of the release button 76 is radially inwardly moved, and the outer cylinder drive surface 84 of the outer cylinder arm portion 83 slides on the shaft drive surface 82 of the button shaft 78, so that the outer cylinder 71 is axially inwardly moved from the connection position to the separation position against the urging by the outside elastic member 66 and kept as it is. As a result, the holding of the steel ball 63 by the outer cylinder holding surface 74 of the outer cylinder 71 at the engaging position is released, and the steel ball 63 is enabled to move to the retraction position.

Referring to FIGS. 3C and 3A and FIGS. 4B and 4A, in order to separate the operation unit 36 from the motor unit 29, the operation unit 36 is moved away from the motor unit 29 in the connecting and separating axial direction. As a result, the plug 43 of the operation unit side connection portion 38 is pulled out from the receptacle 48 of the motor unit side connection portion 37. At the same time, the lock pin 53 of the operation unit side connection portion 38 is pulled out from the inner cylinder 61 of the motor unit side connection portion 37. At this point, the steel ball 63 is moved from the engaging position to the retraction position by the pin retraction surface 58 of the lock pin 53, the stop cylinder 64 is axially outwardly move together with the lock pin 53 due to the urging by the inside elastic member 67, and the outer small outside diameter portion of the stop cylinder 64 is inserted into the middle small inside diameter portion of the inner cylinder 61. At the same time, the limitation pin 86 of the operation unit side connection portion 38 is pulled out from the pin receiving portion 88 of the motor unit side connection portion 37.

In addition, after the lock pin 53 has been pulled out, the stop cylinder 64 is held at the separation position by the inside elastic member 67, and the steel ball 63 is held at the retraction position by the stop cylinder holding surface 68 of the stop cylinder 64. Moreover, the outer cylinder 71 is held at the separation position by the steel ball 63, and the release button 76 remains at the separation position.

The electric bending endoscope 21 in the present embodiment includes the following effects.

In the electric bending endoscope 21 in the present embodiment, the motor unit 29 and the operation unit 36 are locked to each other by the lock mechanism, so that unintentional separation of the motor unit 29 from the operation unit 36 is prevented. Further, the rotation limitation mechanism prevents relative rotation of the motor unit 29 and the operation unit 36. Moreover, the lock pin 53 and the inner cylinder 61 of the lock mechanism are also used as the rotation limitation mechanism, thereby achieving simplification of the configuration, reduction in the number of components, and reduction in costs.

Figure 6:
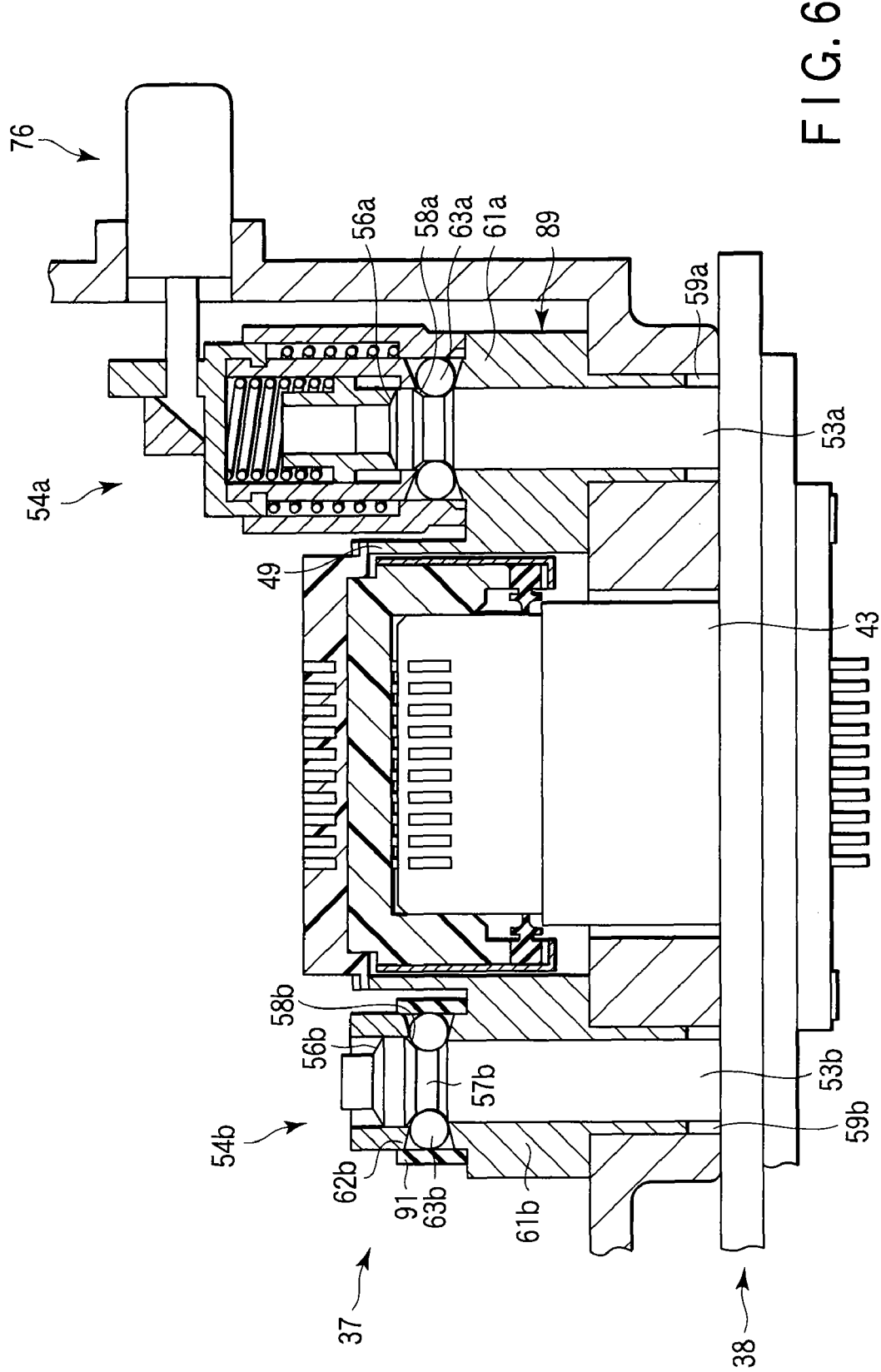
FIG. 6 is a partial longitudinal sectional side view showing a connection and separation mechanism according to a second embodiment of the present invention.

FIG. 6 shows a second embodiment of the present invention.

In a connection and separation mechanism in the present embodiment, an electric connection mechanism similar in configuration to the electric connection mechanism in the first embodiment is used. However, a holder member 89 is used in a motor unit side connection portion 37, and the holder member 89 forms a support portion 49 of a floating mechanism.

In the connection and separation mechanism, a first lock mechanism similar in configuration to the lock mechanism in the first embodiment is used. Hereinafter, components of the first lock mechanism are referred to with "first" added thereto. In a first lock receiving mechanism 54a, the holder member 89 forms a first inner cylinder portion 61a similar in configuration to the inner cylinder 61 in the first embodiment. In the first inner cylinder portion 61a, an outer small outside diameter portion is further formed on axially outside with respect to the outer large outside diameter portion, and the outer small outside diameter portion is fitted in and fixed to a first lock pin insertion hole 59a of the motor unit housing 46.

Furthermore, a second lock mechanism is used in the connection and separation mechanism. The second lock mechanism is formed by a second lock pin 53b as a lock portion provided in an operation unit side connection portion 38, and a second lock receiving mechanism 54b provided in a motor unit side connection portion 37.

That is, the second columnar lock pin 53b protrudes through an operation unit housing 42 in the connection and separation direction. The second lock pin 53b is disposed opposite to a first lock pin 53a with respect to a plug 43. The second lock pin 53b includes the same shape as the first lock pin 53a. However, in the second lock pin 53b, an outer pin retraction surface 56b and an inner pin retraction surface 58b are formed by the surfaces corresponding to a first pin drive surface 56a and a first pin retraction surface 58a of the first lock pin 53a.

In the second lock receiving mechanism 54b, a second lock pin insertion hole 59b is formed through the motor unit housing 46. A second inner cylinder portion 61b as a lock receiving portion formed by the holder member 89 is provided on the inside with respect to the second lock pin insertion hole 59b and extends in the connecting and separating axial direction. The second inner cylinder portion 61b includes an outer small outside diameter portion on the axially outer side thereof, a middle large outside diameter portion on the axially middle portion thereof, and an inner small outside diameter portion on the axially inner side thereof. The outer small outside diameter portion is fitted in and fixed to the second lock pin insertion hole 59b, and the axially outer end surface of the middle large outside diameter portion is fixed to the inner surface of the motor unit housing 46. When an operation unit 36 is moved with respect to a motor unit 29 in the connecting and separating axial direction, the second lock pin 53b of the operation unit side connection portion 38 is inserted into and pulled out from the second inner cylinder portion 61b. The axially inner position of the second lock pin 53b when completely inserted into the second inner cylinder portion 61b is referred to as a connection position. Second container holes 62b radially perforate the inner small outside diameter portion of the second inner cylinder portion 61b. A second steel ball 63b as an engaging member is radially slidably contained in the second container hole 62b in the same manner as a first steel ball 63a. As in the first embodiment, when the second lock pin 53b is disposed at the connection position, a second engagement receiving portion 57b of the second lock pin 53b is aligned with the radial inner end side of the second container hole 62b so that the second steel ball 63b is enabled to engage with and disengage from the second engagement receiving portion 57b. The second steel ball 63b is configured to be disposed at a radially inside engaging position where the second steel ball 63b is engaged with the second engagement receiving portion 57b and a radial outside retraction position where the second steel ball 63b is disengaged from the second engagement receiving portion 57b.

A C-ring shaped elastic member 91 as an urging mechanism is fitted on outside of the inner small outside diameter portion of the second inner cylinder portion 61b. Second steel balls 63b are fixed to the inner peripheral surface of the elastic member 91. The second steel ball 63b is constantly urged toward the engaging position by the elastic member 91.

When the second lock pin 53b of the operation unit side connection portion 38 is inserted into and pulled out from the second inner cylinder portion 61b, the second steel ball 63b is radially outwardly moved from the engaging position to the retraction position by the outer pin retraction surface 56b and the inner pin retraction surface 58b as a retraction mechanism of the second lock pin 53b, respectively.

A rotation limitation mechanism of the connection and separation mechanism is formed by the first and second lock pins 53a, 53b as the first and second limitation members and the first and second inner cylinder portions 61a, 61b as the first and second limitation receiving members. That is, the rotation of the first lock pin 53a around the connecting and separating axis is limited by the first inner cylinder portion 61a, and the rotation of the second lock pin 53b around the same is limited by the second inner cylinder portion 61b, so that the rotation of the operation unit 36 with respect to the motor unit 29 around the same is limited.

Furthermore, a plug protection mechanism is formed in the electric bending endoscope 21. That is, the length of the protrusion of the first and second lock pins 53a, 53b is greater than the length of the protrusion of the plug 43 in the connecting and separating axial direction, and the plug 43 is protected by the first and second lock pins 53a, 53b.

Next, the method of using the electric bending endoscope 21 in the present embodiment is described.

In order to connect the operation unit 36 to the motor unit 29, the operation unit 36 is moved close to the motor unit 29 in the connecting and separating axial direction, as in the first embodiment. In the first lock mechanism, the first lock pin 53a is locked by the first lock receiving mechanism 54a, as in the first embodiment. On the other hand, in the second lock mechanism, the second lock pin 53b of the operation unit side connection portion 38 is inserted into the second inner cylinder portion 61b of the motor unit side connection portion 37, and the second steel ball 63b is moved by the outer pin retraction surface 56b of the second lock pin 53b from the engaging position to the retraction position against the urging by the elastic member 91. Then, when the second lock pin 53b is disposed at the connection position, the second steel ball 63b is engaged with the second engagement receiving portion 57b of the second lock pin 53b due to the urging by the elastic member 91. Thus, the second lock pin 53b is engaged with the second lock receiving mechanism 54b. In addition, when the second lock pin 53b is inserted into the second inner cylinder portion 61b, the second lock pin 53b is constantly held in a sliding state by the second steel balls 63b due to the urging force of the elastic member 91, so that the shaking of the second lock pin 53b with respect to the second inner cylinder portion 61b is prevented, and the shaking of the operation unit 36 with respect to the motor unit 29 is prevented.

As in the first embodiment, the operation unit 36 is operated, so that the endoscope 21 is actuated. In the endoscope 21, the motor unit 29 and the operation unit 36 are locked to each other by the first and second lock mechanisms arranged opposite to each other with respect to the electric connection mechanism, so that the operation unit 36 is sufficiently firmly and stably locked to the motor unit 29. Moreover, even when the release button 76 is erroneously operated to be depressed during the actuation of the endoscope 21, since the operation unit 36 is locked to the motor unit 29 in the connecting and separating axial direction by the second lock mechanism, an unintentional separation of the motor unit 29 from the operation unit 36 is surely prevented.

In order to separate the operation unit 36 from the motor unit 29, the release button 76 is operated to be depressed, and then the operation unit 36 is moved away from the motor unit 29 in the connecting and separating axial direction, as in the first embodiment. In the second lock mechanism, the second steel ball 63b is moved by the inner pin retraction surface 58b of the second lock pin 53b from the engaging position to the retraction position against the urging by the elastic member 91, and the second lock pin 53b is pulled out from the second inner cylinder portion 61b.

In addition, even when the operation unit 36 is bumped against the motor unit 29 or dropped, for example, during connection or separation, the first and second lock pins 53a, 53b bump against the motor unit 29 or the floor before the plug 43 bumps against the motor unit 29 or the floor, so that the plug 43 is protected.

The electric bending endoscope 21 in the present embodiment includes the following effects.

In the electric bending endoscope 21 in the present embodiment, the first and second lock mechanisms are used, so that it is possible to sufficiently firmly and stably lock the operation unit 36 to the motor unit 29. Moreover, since the release mechanism for unlocking the motor unit 29 and the operation unit 36 from each other is not employed in the second lock mechanism, the operation unit 36 is prevented from being moved apart from the motor unit 29 even when the lock of the motor unit 29 and the operation unit 36 by the first lock mechanism are erroneously released.

Furthermore, it is possible for the protection mechanism to protect the plug 43.

Moreover, the first and second lock pins 53a, 53b and the first and second inner cylinder portions 61a, 61b of the lock mechanism form the rotation limitation mechanism, and the first and second lock pins 53a, 53b of the lock mechanism and the rotation limitation mechanism forms the protection mechanism, thereby achieving simplification of the configuration, the reduction of the number of components, and the reduction of costs. Further, the first and second inner cylinder portions 61a, 61b and the support portion 49 are formed by the integral holder member 89, thereby achieving simplification of the configuration, reduction in the number of components, and reduction in costs. Moreover, centering and positioning are facilitated, thereby improving reliability.

It is noted that a lock mechanism similar to the first lock mechanism may be used as the second lock mechanism. In this case, a common release button may be used to release the locking by the first and second lock mechanisms.

Figure 7:
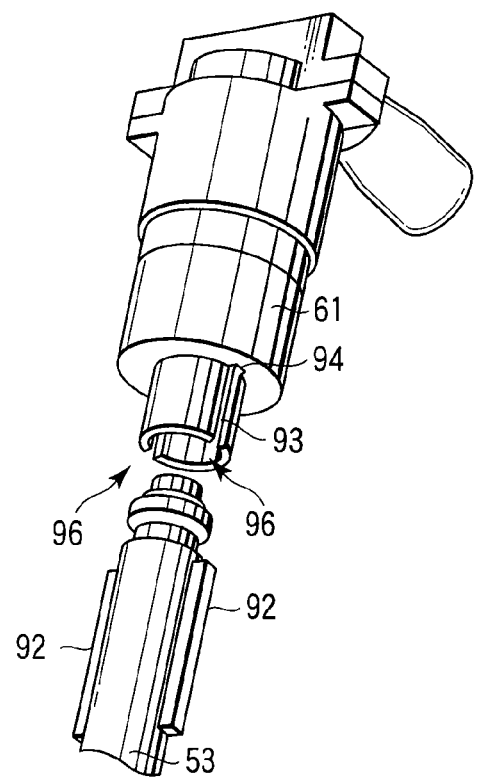
FIG. 7 is a perspective view showing a rotation limitation mechanism according to a third embodiment of the present invention.

FIG. 7 shows a third embodiment of the present invention.

A connection and separation mechanism in the present embodiment includes a lock mechanism similar to the first lock mechanism in the second embodiment. The lock mechanism includes an inner cylinder 61 similar in configuration to the first inner cylinder portion 61a in the second embodiment.

With regard to a rotation limitation mechanism, a pair of ribs 92 as a limitation portion are formed in the inner large outside diameter portion of a first lock pin 53a as a limitation member in an operation unit side connection portion 38. The pair of ribs 92 project radially outwardly, extend in the axial direction of the lock pin 53, and are arranged symmetrically to each other with respect to the central axis of the lock pin 53. On the other hand, in a motor unit side connection portion 37, a pair of slits 93 are formed in the outer small outside diameter portion of the inner cylinder 61 as limitation receiving members, extend in the axial direction of the inner cylinder 61, and are symmetrical to each other with respect to the central axis of the inner cylinder 61. Further, pair of grooves 94 are formed in the inner peripheral surface of the outer large outside diameter portion of the inner cylinder 61, and the pair of grooves 94 are continuous with the pair of slits 93 and extend in the axial direction of the inner cylinder 61. The pair of slits 93 and the pair of grooves 94 form a pair of limitation groove portions 96 as limitation receiving portions. When the lock pin 53 is inserted into and pulled out from the inner cylinder 61, the pair of ribs 92 of the lock pin 53 are inserted into and pulled out from the pair of limitation groove portions 96 of the inner cylinder 61, respectively, and the pair of ribs 92 are axially slidable in the pair of limitation groove portions 96. When the lock pin 53 is inserted in the inner cylinder 61 and disposed at the connection position, the pair of ribs 92 of the lock pin 53 are inserted in the pair of limitation groove portions 96 of the inner cylinder 61, and the rotation of the pair of ribs 92 around the central axis of the lock pin 53 is limited by both side surfaces of the limitation groove portions 96, so that the rotation of the lock pin 53 is limited. Thus, the rotation of the operation unit 36 with respect to the motor unit 29 around the connecting and separating axis is limited.

The electric bending endoscope 21 in the present embodiment includes the following effects.

In the electric bending endoscope 21 in the present embodiment, in contrast with the first and second embodiments, the rotation limitation mechanism only uses the integral mechanism without using a pair of mechanisms provided separately from each other, such as the lock pin and the inner cylinder and the limitation pin and the pin receiving portion, thereby achieving simplification of the configuration, reduction in the number of components, and reduction in costs.

Figure 8A:
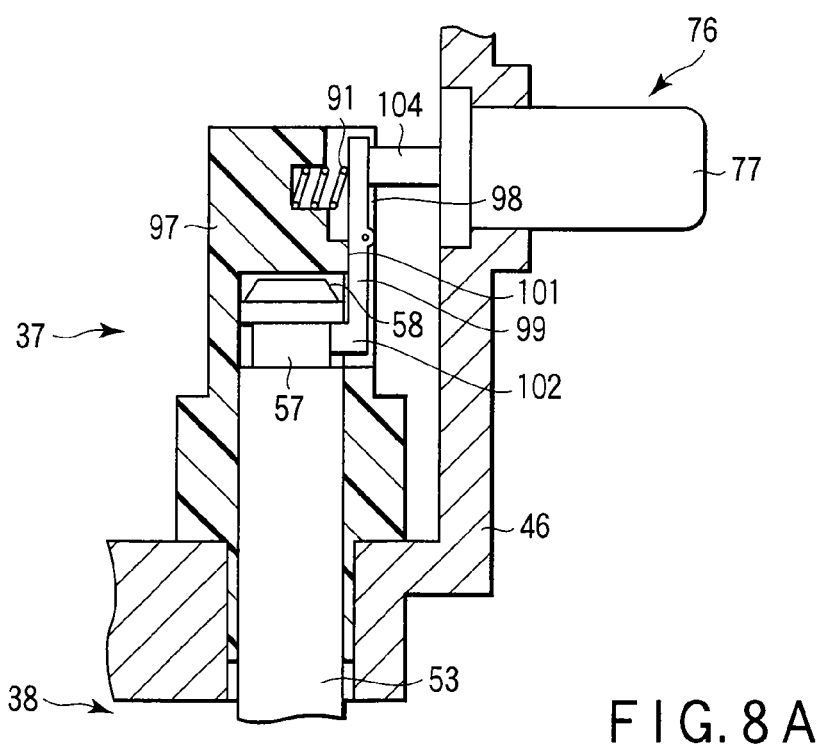
FIG. 8A is a partial longitudinal sectional side view showing a lock mechanism according to a fourth embodiment of the present invention in a connection state.
Figure 8B:
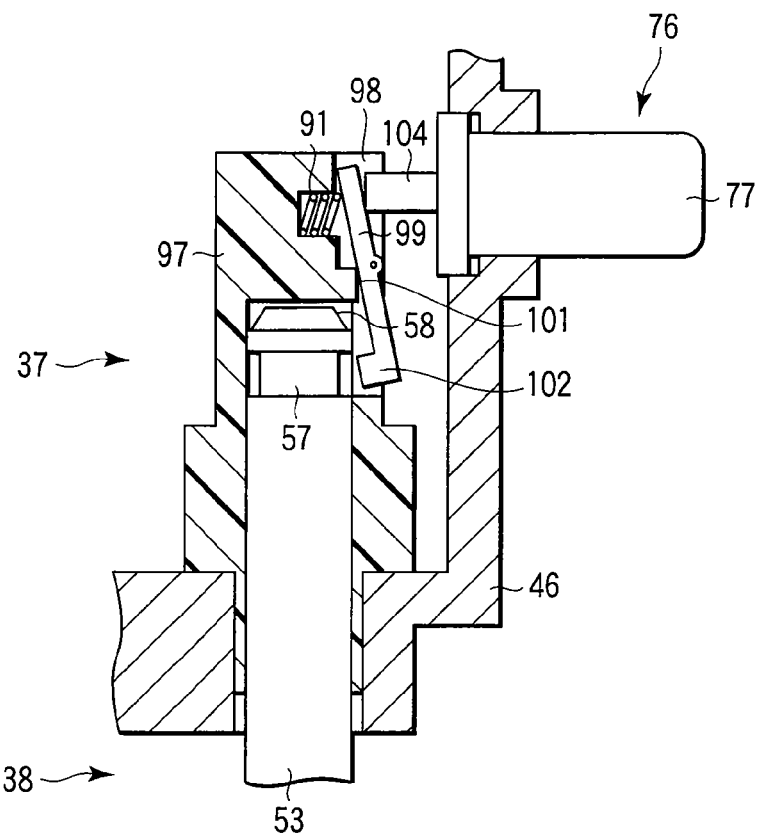
FIG. 8B is a partial longitudinal sectional side view showing the lock mechanism according to the fourth embodiment of the present invention in a separation state.

FIGS. 8A and 8B show a fourth embodiment of the present invention.

In a lock mechanism in the present embodiment, an axially outwardly and radially inwardly inclined pin retraction surface 58 is formed at the outer end of a lock pin 53 as a lock portion. Further, a groove shaped engagement receiving portion 57 circumferentially extends on the outer end portion of the lock pin 53.

In a lock receiving mechanism 54, a lock pin insertion hole 59 is formed through a motor unit housing 46 in a motor unit side connection portion 37. A cylindrical pin holder 97 as a lock receiving portion is provided on the inside with respect to the lock pin insertion hole 59 and extends in the connecting and separating axial direction. The pin holder 97 includes an outer small outside diameter portion on the axially outer side thereof, a middle large outside diameter portion on the axially middle portion thereof, and an inner small outside diameter portion on the axially inner side thereof. The outer small outside diameter portion is fitted in and fixed to the lock pin insertion hole 59, and the axially outer end surface of the middle large outside diameter portion is fixed to the inner surface of the motor unit housing 46. When an operation unit 36 is moved with respect to a motor unit 29 in the connecting and separating axial direction, the lock pin 53 of an operation unit side connection portion 38 is inserted into and pulled out from the pin holder 97 via the lock pin insertion hole 59. The axially inner position of the lock pin 53 when completely inserted into the pin holder 97 is referred to as a connection position.

In the inner small outside diameter portion of the pin holder 97, the axially inner end side thereof is solid. A container groove 98 axially extends in the outer peripheral portion of the inner small outside diameter portion. A plate shaped anti-pull member 99 as an engaging member axially extends in the container groove 98. The axially middle portion of the anti-pull member 99 is pivotally attached to the pin holder 97, and the anti-pull member 99 is rotated around a rotational axis perpendicular to the axial direction. A coil shaped inside elastic member 91 as an urging mechanism is compressively provided between the axially inner end portion of the anti-pull member 99 and the bottom portion of the container groove 98 of the pin holder 97, and the axially inner portion of the anti-pull member 99 is constantly radially outwardly urged, while the axially outer portion of the anti-pull member 99 is constantly radially inwardly urged. A holder limiting surface 101 is formed in the pin holder 97 and faces the axially outer portion of the anti-pull member 99. When the axially outer portion of the anti-pull member 99 comes into contact with the holder limiting surface 101, the radially inward movement of the axially outer portion of the anti-pull member 99 is limited. This position of the anti-pull member 99 is referred to as an engaging position. An anti-pull claw 102 protrudes radially inwardly from the axially outer end portion of the anti-pull member 99. Here, the axially outer end portion of the container groove 98 is in communication with the inner cavity of the pin holder 97. When the lock pin 53 of the operation unit side connection portion 38 is at the connection position and the anti-pull member 99 is at the engaging position, the anti-pull claw 102 is engaged with the engagement receiving portion 57 of the lock pin 53.

when the lock pin 53 is inserted into the pin holder 97 in the state where the anti-pull member 99 is at the engaging position, the anti-pull claw 102 of the anti-pull member 99 is pressed by the pin retraction surface 58 of the lock pin 53 as a retraction mechanism and thus radially outwardly moved, and the anti-pull member 99 is rotated to the retraction position.

A release button 76 as a release mechanism is provided in the motor unit housing 46. The release button 76 is slidable in the radial direction of the pin holder 97, and is configured to be disposed at the radially outside connection position and the radially inside release position. That is, the button cap 77 of the release button 76 is configured to project and depress in the radial direction of the pin holder 97. A shaft portion 104 protrudes radially inwardly from the radially inner end portion of the button cap 77. When the release button 76 is at the connection position, the inner end portion of the shaft portion 104 is in contact with the radial outside of the axially inner end portion of the anti-pull member 99 at the engaging position. When the release button 76 is radially inwardly moved to the release position, the axially inner end portion of the anti-pull member 99 is radially inwardly pressed and moved by the shaft portion 104, and the anti-pull member 99 is rotated to the release position. When the lock pin 53 of the operation unit side connection portion 38 is disposed at the connection position and the anti-pull member 99 is at the release position, the engagement of the engagement receiving portion 57 of the lock pin 53 and the anti-pull claw 102 of the anti-pull member 99 is released.

Next, the connection and separation operation of the electric bending endoscope 21 in the present embodiment is described.

In order to connect the operation unit 36 to the motor unit 29, the operation unit 36 is moved close to the motor unit 29 in the connecting and separating axial direction. As a result, the lock pin 53 of the operation unit side connection portion 38 is inserted into the pin holder 97 via the lock pin insertion hole 59 of the motor unit side connection portion 37. At this point, the anti-pull claw 102 of the anti-pull member 99 is pressed and radially outwardly moved by the pin retraction surface 58 of the lock pin 53, and the anti-pull member 99 is rotated to the retraction position, and the lock pin 53 is inserted to the connection position. When the lock pin 53 is disposed at the connection position, the anti-pull claw 102 of the anti-pull member 99 is engaged with the engagement receiving portion 57 of the lock pin 53 due to the urging by the elastic member 91. Thus, the lock pin 53 is locked to the lock receiving mechanism 54, and the operation unit 36 is locked to the motor unit 29 with respect to the connecting and separating axial direction.

In order to separate the operation unit 36 from the motor unit 29, the release button 76 is operated to be depressed. As a result, the axially inner end portion of the anti-pull member 99 is radially inwardly pressed and moved by the shaft portion 104 of the release button 76, and the anti-pull member 99 is rotated to the release position, and the engagement of the engagement receiving portion 57 of the lock pin 53 and the anti-pull claw 102 of the anti-pull member 99 is released. Thus, the lock pin 53 is enabled to be pulled out from the pin holder 97, and the operation unit 36 is enabled to be moved apart from the motor unit 29. Then, the operation unit 36 is moved away from the motor unit 29 in the connecting and separating axial direction, and the operation unit 36 is moved apart from the motor unit 29.

The electric bending endoscope 21 in the present embodiment includes the following effects.

In the electric bending endoscope 21 in the present embodiment, the lock mechanism includes an extremely simple configuration, thereby achieving a reduction in the number of components and a reduction in costs.

Figure 9:
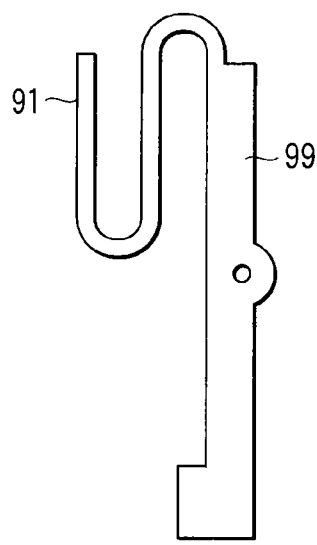
FIG. 9 is a side view showing an anti-pull member according to a first modification of the fourth embodiment of the present invention.

FIG. 9 shows a first modification of the fourth embodiment of the present invention.

In the present modification, a leaf-spring shaped elastic member 91 integral with the anti-pull member 99 is used instead of the coil shaped elastic member 91.

A second modification of the fourth embodiment of the present invention is described below.

In the present modification, a square columnar lock pin 53 as a limitation member and a square cylindrical pin holder 97 as a limitation receiving member are used as a rotation limitation mechanism. When the square columnar lock pin 53 is inserted into the square cylindrical pin holder 97, the rotation of the lock pin 53 with respect to the pin holder 97 around the central axis of the lock pin 53 is limited, so that the rotation of the operation unit 36 with respect to the motor unit 29 around the connecting and separating axis is limited. In the present modification, the lock mechanism is integrated with the rotation limitation mechanism, which provides a sufficiently simple configuration, thereby achieving a reduction in the number of components and a reduction in costs.

Figure 10A:
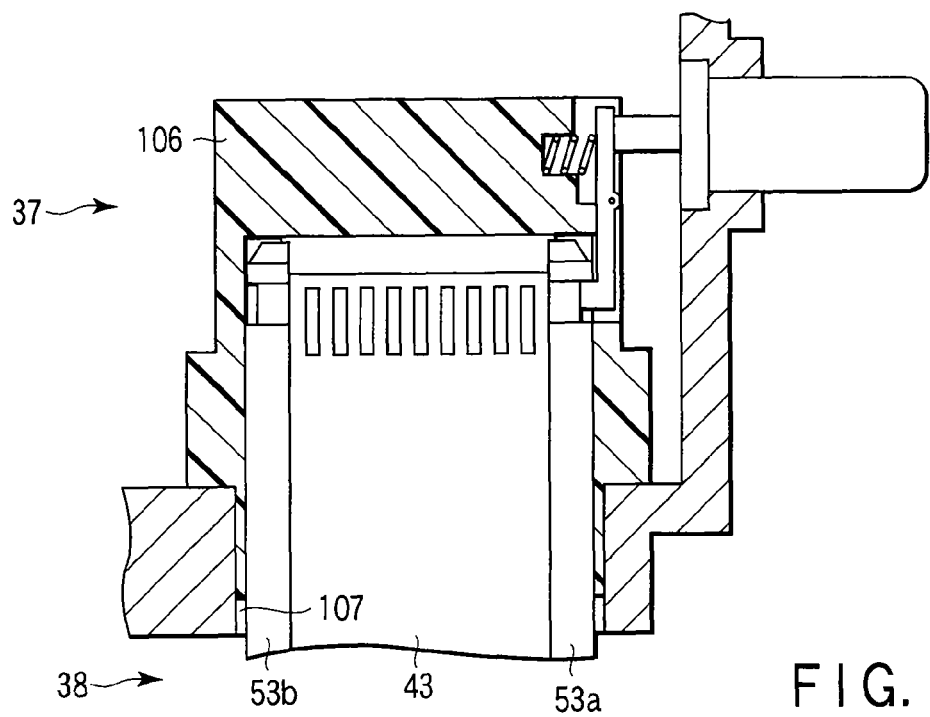
FIG. 10A is a partial longitudinal sectional side view showing a lock mechanism according to a fifth embodiment of the present invention in a connection state.
Figure 10B:
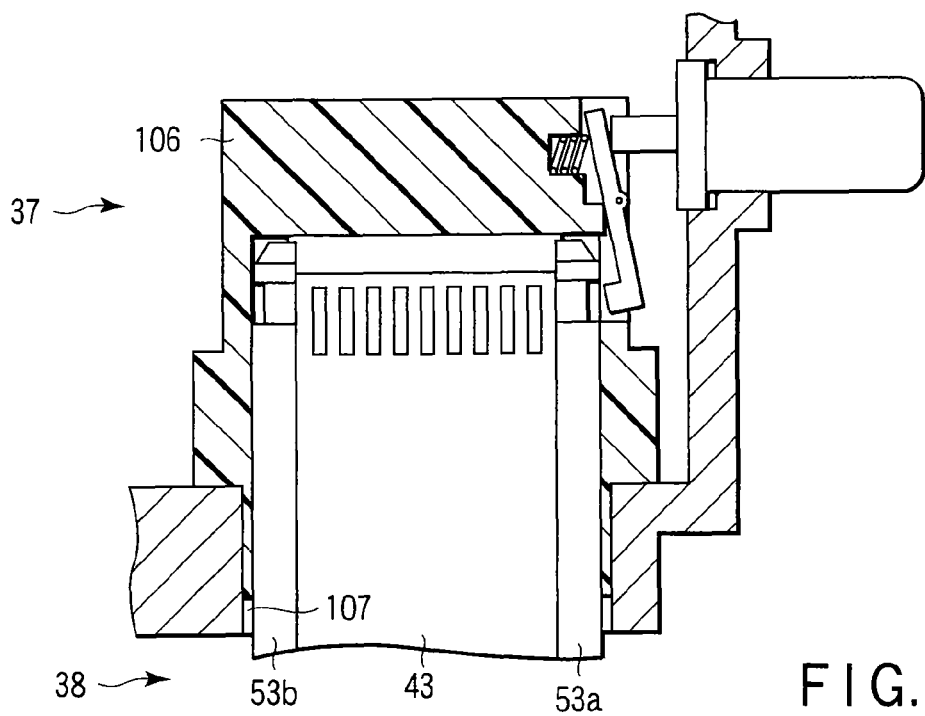
FIG. 10B is a partial longitudinal sectional side view showing the lock mechanism according to the fifth embodiment of the present invention in a separation state.
Figure 11:
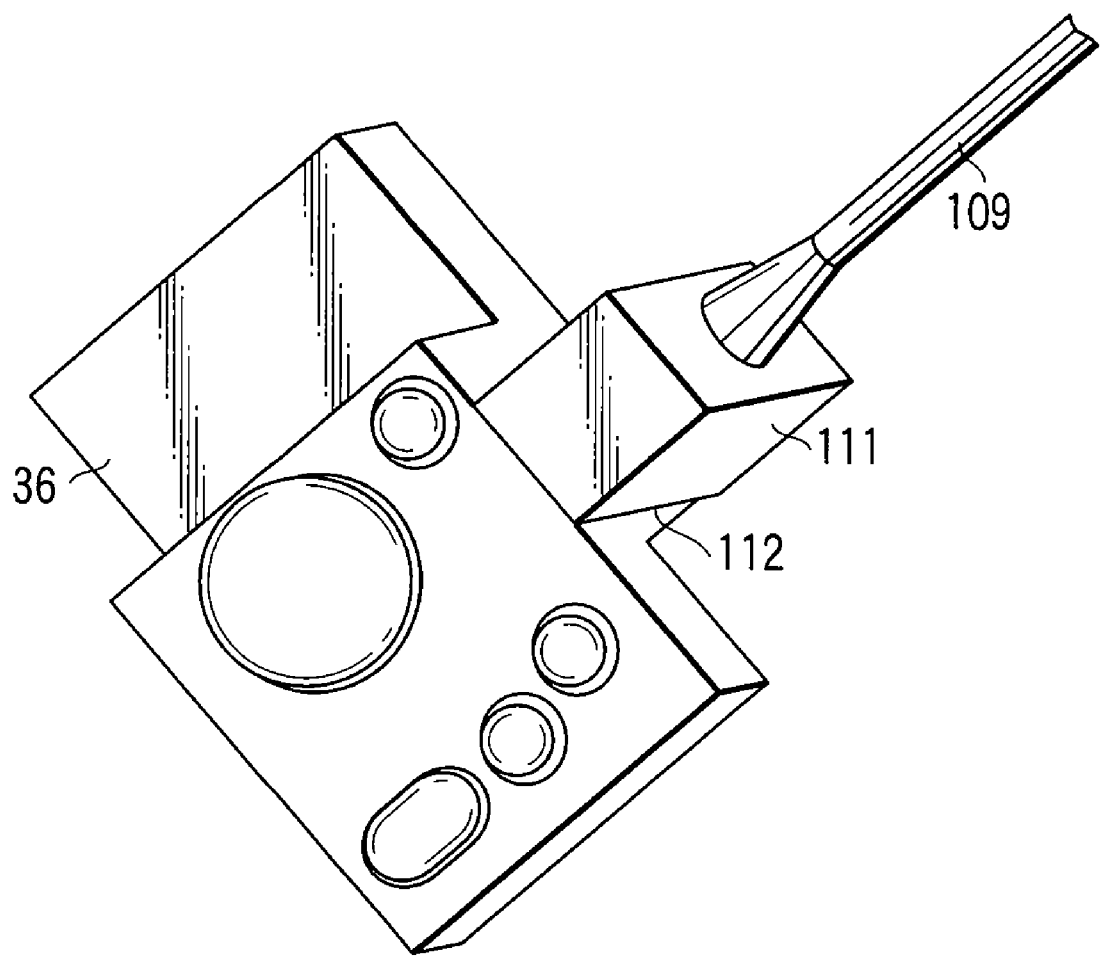
FIG. 11 is a perspective view showing an operation cord and an operation unit according to a reference embodiment of the present invention.

FIGS. 10A and 10B show a fifth embodiment of the present invention.

In an electric connection mechanism and a lock mechanism of the present embodiment, first and second lock pins 53a, 53b extend in the connecting and separating axial direction along two narrow side surfaces of a plug 43 in an operation unit side connection portion 38, respectively. The first and second lock pins 53a, 53b includes such a shape that the lock pin 53 in the fourth embodiment is divided into two parts along the central axis. The flat portions of the first and second lock pins 53a, 53b face the two narrow side surfaces of the plug 43, respectively. In addition, the length of the protrusion of the first and second lock pins 53a, 53b is greater than the length of the protrusion of the plug 43 in the connecting and separating axial direction, and a protection mechanism is formed by the first and second lock pins 53a, 53b.

In a motor unit side connection portion 37, a joint insertion hole 107 is formed through a motor unit housing 46. A cylindrical joint holder 106 is provided on the inside with respect to the joint insertion hole 107 and extends in the connecting and separating axial direction. The axially outer end portion of the joint holder 106 is fixed to the inner surface of the motor unit housing 46. In a section perpendicular to the connecting and separating axial direction, the inner peripheral shape of the joint holder 106 is substantially coincident with the outer peripheral shape of the plug 43 and the first and second lock pins 53a, 53b of the operation unit side connection portion 38. When an operation unit 36 is moved with respect to a motor unit 29 in the connecting and separating axial direction, the plug 43 and the first and second lock pins 53a, 53b is inserted into and pulled out from the joint holder 106 via the joint insertion hole 107. The axially inner position of the plug 43 and the first and second lock pins 53a, 53b when completely inserted into the joint holder 106 is referred to as a connection position. The axially inner end side of the joint holder 106 is solid, and is provided with an unshown receptacle contact.

Furthermore, a lock mechanism similar in configuration to that in the fourth embodiment is formed in the first lock pin 53a.

Moreover, with regard to a rotation limitation mechanism, a combination of the plug 43 and the first and second lock pins 53a, 53b form a limitation member, and the first and second lock pins 53a, 53b form a limitation portion. On the other hand, the joint holder 106 forms a limitation receiving member, and the inner surfaces of both sides of the joint holder 106 form a limitation receiving portion. Further, the rotation of the first and second lock pins 53a, 53b around the connecting and separating axis is limited by the inner surfaces of both sides of the joint holder 106, so that the rotation of the operation unit 36 with respect to the motor unit 29 around the same is limited.

The electric bending endoscope 21 in the present embodiment includes the following effects.

In the electric bending endoscope 21 in the present embodiment, the electric contact mechanism, the lock mechanism and the rotation limitation mechanism are integrated, which provides an extremely simple configuration, thereby achieving a reduction in the number of components and a reduction in costs.

In addition, a lock mechanism similar in configuration to that in the fourth embodiment may be formed in the second lock pin 53b. Moreover, a common release button may be used for a first lock mechanism of the first lock pin 53a and a second lock mechanism of the second lock pin 53b.

A reference embodiment of the present invention is described with reference to FIGS. 1 to 11.

In an electric bending endoscope system of the reference embodiment, a system controller 108 is connected to the video processor 33. An operation cord 109 extends from the system controller 108. An operation cord connector 111 is provided at the extending end of the operation cord 109, and the operation cord connector 111 is provided with an operation cord side connection portion 112 similar in configuration to the motor unit side connection portion 37. When the operation unit side connection portion 38 of the operation unit 36 is connected to the operation cord side connection portion 112, the operation unit 36 is connected to the operation cord connector 111. Further, when the operation unit 36 connected to the operation cord connector 111 is operated, the endoscope 21 is actuated.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. An electric bending endoscope comprising:
   an elongate insertion portion configured to be inserted into a lumen and provided with a bending portion configured to be actuated to be bent;
   a drive unit connected to a proximal end portion of the insertion portion and configured to generate a drive force to actuate the bending portion to bend; and
   an operation unit configured to be held by an operator and operate at least a bending actuation of the bending portion,
   wherein the drive unit and the operation unit respectively include a drive unit side electric contact portion and an operation unit side electric contact portion configured to be coupled to and separated from each other by moving the drive unit and the operation unit close to and apart from each other in a coupling and separating axial direction, and
   the drive unit and the operation unit includes a lock mechanism configured to lock and unlock the drive unit and the operation unit to and from each other with respect to the coupling and separating axial direction,
   wherein the lock mechanism includes:
   a lock portion provided in one of the drive unit and the operation unit; and
   a lock receiving mechanism provided in the other of the drive unit and the operation unit, the lock portion is configured to be inserted into and pulled out from the lock receiving mechanism by moving the drive unit and the operation unit close to and apart from each other in the coupling and separating axial direction, and
   the lock receiving mechanism is configured to lock the lock portion inserted into the lock receiving mechanism, and
   wherein the lock receiving mechanism includes:
   a lock receiving portion wherein the lock portion is configured to be inserted into and pulled out from the lock receiving portion;
   an engaing member configured to move between an engaing position where the engaging member engages with the lock portion and a retraction position where the engaging member enables the lock portion to be inserted into and pulled out from the lock receiving portion;
   a holding mechanism configured to be switched between a holdin state where the holdin mechanism holds the engaging member at the retraction position and a free state where the holding mechanism frees the engaging member wherein the holding mechanism is configured to be in the holding state when the lock portion is not inserted in the lock receiving portion; and
   an urging mechanism configured to urge the engaging member toward the engaging position; and
   the lock portion includes:
   a free mechanism configured to switch the holding mechanism from the holding state to the free state in conjunction with an inserting action of the lock portion.

2. The electric bending endoscope according to claim 1, wherein the lock receiving mechanism includes:
   a release mechanism configured to release the urging to the engaging member by the urging mechanism, and the lock portion includes:
   a retraction mechanism configured to move the engaging member to the retraction position in conjunction with a pulling-out action of the lock portion.

* * * * *